United States Patent [19]

Chadwick

[11] Patent Number: 5,571,125
[45] Date of Patent: Nov. 5, 1996

[54] PENIS-CLAMPING DEVICE FOR THE INCONTINENT

[76] Inventor: Dale A. Chadwick, 960 Northwood Dr., Endwell, N.Y. 13760

[21] Appl. No.: 512,063

[22] Filed: Aug. 7, 1995

[51] Int. Cl.[6] ............................................ A61B 17/08
[52] U.S. Cl. ..................... 606/157; 606/151; 606/158; 128/DIG. 25
[58] Field of Search ..................... 606/157, 158, 606/151, 140, 141, 143; 128/843, DIG. 25; 24/514, 502, 569

[56] References Cited

U.S. PATENT DOCUMENTS

| | | | |
|---|---|---|---|
| 2,925,682 | 2/1960 | Kravitch | 24/502 |
| 3,155,096 | 11/1964 | Outwin | 128/885 |
| 3,203,421 | 8/1965 | Bialick | 128/DIG. 25 |
| 3,866,611 | 2/1975 | Baumrucker | 128/DIG. 25 |
| 4,139,007 | 2/1979 | Diamond | 128/842 |
| 4,390,019 | 6/1983 | LeVeen et al. | 606/158 |
| 4,942,886 | 7/1990 | Timmons | 128/885 |

*Primary Examiner*—Michael Powell Buiz
*Assistant Examiner*—Kevin Truong
*Attorney, Agent, or Firm*—Salzman & Levy

[57] ABSTRACT

The present invention features a device to prevent the unwanted flow of urine in incontinent human males. This penile clamp is designed to provide safety and comfort to the user, while restricting involuntary urine flow. This device includes a cushioned, easily disinfected clamp that is hinged at one end and provided with an adjustable tensioning closure device at its other end. Designed as a hinged clamshell, the penis clamp is easily openable by one-handed pressure release. This screw-type adjustment is easily set and is easily disassembled by a quick-release apparatus. While the clamp can be closed over the penis of an incontinent male to prevent urination, it does not appreciably restrict blood flow therein.

5 Claims, 1 Drawing Sheet

PENIS-CLAMPING DEVICE FOR THE INCONTINENT

FIELD OF THE INVENTION

The present invention pertains to a device for restricting the flow of urine through the penis of an incontinent human male and providing for the voluntary release of urine, and, more particularly, to an easily adjustable, penis-clamping apparatus for incontinent males.

BACKGROUND OF THE INVENTION

While male incontinence is a common and often neglected problem, the distress, embarrassment and inconvenience imposed on individuals suffering from involuntary urination warrants the development of non-invasive solutions to this condition.

To date, the common means of preventing the involuntary flow of urine in incontinent males has been to clamp the penis via a device that becomes painful, socially restrictive and difficult to keep clean. Such devices cause pressure to be applied upon the urethra, which consequently restricts the flow of urine through the penis.

U.S. Pat. No. 4,942,886 (entitled "External Incontinency Device" and issued to TIMMONS on Jul. 24, 1990) discloses a device having rigid members hinged together at one end and a rachet portion with a plurality of recesses. When a strap is placed in one of the recesses, the two halves of the device are caused to maintain a predetermined position of clamping the penis. Unfortunately, due to the nature of the rachet recess portion, inadvertent pressure against one or both of the sides of the device can cause a tightening of the device and a subsequent, excessive or pathological constriction of the penis.

One of the more popular devices for treating male incontinence is sold under the trademark Bard Cunningham Clamp®. This device, too, has a rachet-type closure mechanism that is subject to the same types of difficulties regarding any inadvertent bumping or touching thereof.

While not specifically addressing incontinence, U.S. Pat. No. 4,139,007 (entitled "Method and Apparatus for Conception" and issued to DIAMOND on Feb. 13, 1979) also discloses a male contraceptive device which prevents the leakage of semen into the female vagina. This device also has a rachet recess portion, which is also subject to the same problems as experienced with TIMMONS.

To substitute for the rachet mechanism, Velcro® has been used in various devices. For example, U.S. Pat. Nos. 3,155,096 and 3,866,611 both feature the use of Velcro® fasteners as the closure mechanism. (The former, entitled "Male Incontinence Clamp" issued to OUTWIN on Nov. 3, 1964; the latter, entitled "Incontinence Device", issued to BAUMRUCKER on Feb. 18, 1975.) Unfortunately, as lint and other foreign materials become embedded in the operating mechanism (i.e., hooks and eyes) of the material, Velcro® has a tendency to become less efficient. Over a period of time, therefore, such devices become less useful.

U.S. Pat. No. 3,203,421 (entitled "Incontinence Clamp Device" and issued to BIALICK on Aug. 31, 1965) discloses a device in which a knurled knob is used to tighten together the two portions of the hinged device. The tension appears to be predetermined, and the release of the penis is accomplished by completely removing the device, thus making use thereof at a urinal impossible. Two hands are required to reposition the device. While trying to operate the device, there is also a certain risk involved in dropping any of the parts thereof.

The foregoing approaches to alleviating the problem of urinary incontinence in men leave much to be desired, since these designs offer little in the way of comfort or convenience for the user. In addition, none of these clamps is easy to clean, and none is capable of adjusting pressure upon the urethra. It should be obvious to the casual observer that such devices are neither comfortable nor efficient in resolving the problems imposed by an incontinent condition. In fact, such clamps are sometimes not only unworkable, but are actually dangerous when residual urine burns the skin or when inadvertent tightening causes penile constriction.

There is a need for an improved penile clamp that is safe, comfortable, easily cleanable and more socially practical (i.e., utilizing one-handed operation) than that heretofore devised.

Furthermore, the contemplated apparatus should also provide for the ease of attachment and usage.

Another object of such an apparatus should be the provision for the infinitely variable adjustment of applying different pressures to accommodate the individual needs of users.

Still another objective of the apparatus should be to prevent the absorption of urine by absorptive materials (pads) and, therefore, to promote health and cleanliness.

The present invention comprises a hinged penile clamp that is designed as a clamshell that easily opens and closes. For user comfort, each of the jaws of the clamshell is padded with closed-cell non-liquid visco elastic polymer such as PQ® registered to Rieckens, Inc. The inventive clamp is designed to allow for precise pressure application by employing a screw-type, tightening adjustment for the jaws. The screw-type adjustment is easily set, and is easily disassembled by means of a quick-release apparatus. Despite its being easily disassembled, the adjustment apparatus will not permanently change as a result of accidental manipulation or external forces. In addition, will not accidentally release.

SUMMARY OF THE INVENTION

The present invention pertains to a penile clamp for incontinent males. The clamp is designed to provide safety and comfort to the user, while restricting involuntary urine flow. The penis clamp combines in its design all of the needed improvements to make a reliable, comfortable device that will not cause harm by restricting blood flow. The penis clamp is designed as a hinged clamshell, easily openable by one-handed pressure release. Each of the jaws of the hinged clamshell is padded with closed-cell non-liquid visco elastic polymer so as to provide user comfort and ease of cleanliness. The inventive clamp is designed to allow for precise pressure application by employing a screw-type tightening adjustment for the jaws thereof. This screw-type adjustment is easily set and is easily disassembled by means of a quick-release apparatus. Despite its being easily disassembled, the adjustment apparatus will not permanently change as a result of accidental manipulation or external forces. In addition, the apparatus can be adjusted by the user under varying circumstances.

The invention features materials which are nonporous, and, thus, will not absorb urine itself. The materials, many of which are plastic, allow for ease of cleaning, as well as a reduction in the cost of manufacture (in contrast to the prior art).

BRIEF DESCRIPTION OF THE DRAWINGS

The objects of this invention will become more apparent, and will be better understood with reference to the subsequent detailed description considered in conjunction with the accompanying drawings, in which.

For purposes of clarity and brevity, like elements and components will bear the same numerical designations throughout the FIGURES.

DESCRIPTION OF THE PREFERRED EMBODIMENT

Generally speaking, the invention features a penis clamp for incontinent males. The clamp is designed to provide reduced or limited urine flow, while not restricting blood flow. The penis clamp of the invention is designed as a hinged clamshell, in which the user's penis is inserted therebetween. Thereafter, the two jaws of the clamp are fixed about the penis, causing pressure to be exerted upon the urethra. The pinched urethra will cause a cessation of urine flow through the penis, thus eliminating involuntary urination. The pressure is adjusted to restrict the flow of urine, but not to impair or appreciably restrict the flow of blood in the penis.

Figure 1:
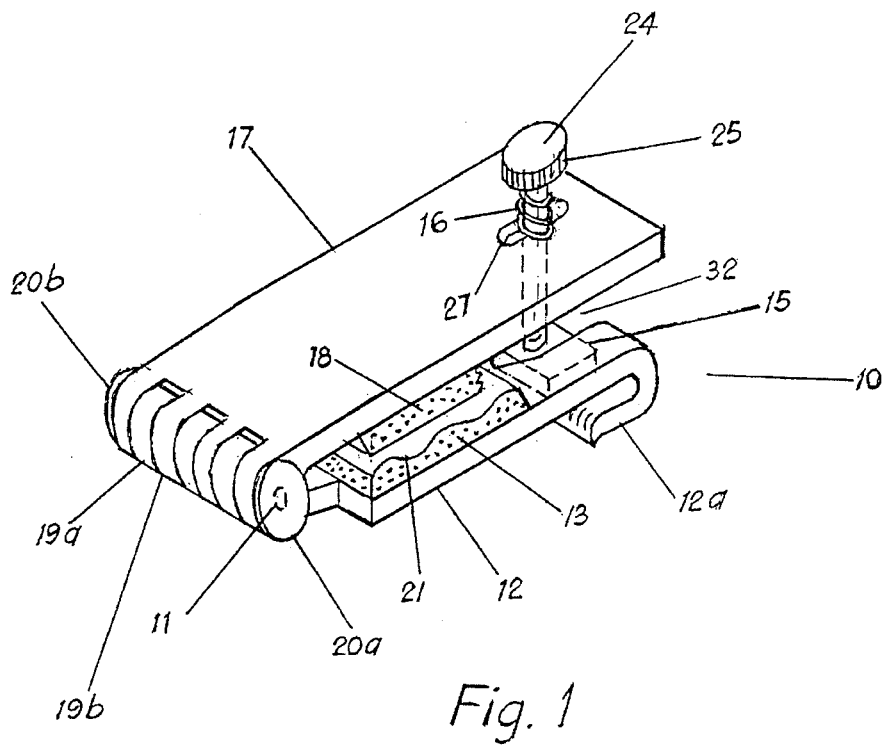
FIG. 1 is a perspective view of the penis clamp of this invention, illustrated in a closed position.
Figure 2:
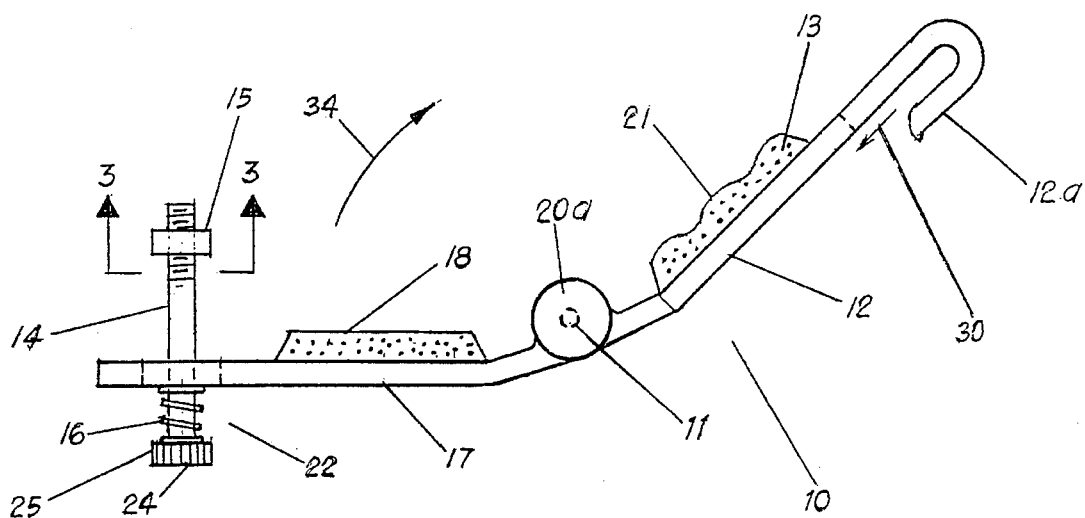
FIG. 2 shows a side view of the penis clamp shown in FIG. 1, illustrated in an open position.

Referring now to FIGS. 1 and 2, a penis clamp 10 is illustrated in its closed position. The penis clamp 10 comprises two clamping jaws respectively represented by extension arms 12 and 17. The jaws 12 and 17 are joined at a common hinge pin 11, about which they rotate. The ends of each respective extension arm 12 and 17 are formed in alternating, interdigitated slots 19a and 19b, respectively, in order to facilitate their rotation about the common hinge pin 11 and with respect to each other. The hinge pin 11 has respective circular flanges 20a and 20b disposed about its distal ends, in order to sandwich the respective extension arms 12 and 17 against lateral movement with respect to hinge pin 11.

Each jaw 12 and 17, respectively, is provided with closed-cell non-liquid visco elastic polymer material or pad 13, which is bonded to the surface of jaw 12 by using waterproof adhesives, if necessary. The pad 13 has an undulate surface 21 disposed in a manner designed to align and apply pressure against the urethra of a penis (not shown) disposed between jaws 12 and 17. Jaw 17 is provided with a substantially flat complementary pad 18 that is likewise bonded to its surface by waterproof adhesives.

The pads 13 and 18 sandwich the penis therebetween and effectively squeeze the user's urethra shut, preventing the passage of urine. The proper pressure to restrict the urethra without interfering with blood flow is a necessary requirement of a safe clamping device. The required pressure is maintained by means of a spring-like, pressure setting closure 22.

The proper pressure is applied to the penis through spring 16, which presses against jaw 17. The spring pressure between jaws 12 and 17 is adjusted by a screw 14 which is threaded into bar 15. The screw 14 is threaded into bar 15 by means of the adjustment knob 24. The adjustment knob 24 has a knurled surface 25 for providing a good gripping surface. The knob 24 of screw 14 restrains the spring 16 against the jaw 17. As the screw 14 is turned in the bar 15 by knob 24, the spring 16 will be compressed, thus forcing the jaws 12 and 17 into compressive union about a penis disposed therebetween. The screw 14 is adjusted by turning clockwise to increase the pressure between the jaws 12 and 17, or counterclockwise to relieve the pressure therebetween. The bar 15 is restrained from rotative movement with the turning of screw 14, by means of a pair of U-shaped tongues 12a disposed upon the end of jaw 12. The bar 15 is removable therefrom by pivoting it out of the tongues 12a, as shown by arrow 30. This removal of bar 15 from between tongues 12a allows the separation of the jaws 12 and 17, as illustrated in FIG. 2. The pivoting of the bar 15 is accomplished by compressing the spring 16, at which time the bar 15 can be moved from between the tongues 12a. A slot 32 disposed in jaw 12 and a slot 27 in jaw 17 allow the screw 14 and bar 15 to be moved into and out of the tongues 12a.

Figure 3:
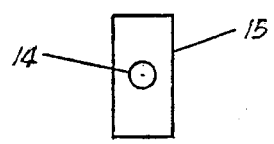
FIG. 3 is a sectional view of the inventive penis clamp, taken along line 3—3 of FIG. 2.

Referring to FIG. 3, a sectional view of the bar 15 and screw 14 is shown.

The compressive pressure exerted upon the urethra by respective clamping jaws 12 and 17 is adjustable by the user by pressure setting closure 22. Sufficient pressure is adjusted and maintained by closure 22, in order to restrict a user's urine flow without seriously restricting his blood flow. The periodic release of the closure 22 is effected at those times when the user feels the need to urinate.

Almost all of the components (and, in particular, elements 11 through 18) can be made from plastic, such as closed-cell polypropylene, styrene, abs cycolac, etc., so as to create lower manufacturing costs and facilitate cleaning.

Once the appropriate pressure is set by means of screw 16 and knurled knob 24, the clamp 10 is attached by the user (not shown) at the base of the penis (not shown). The two jaws 12 and 17 are brought into a substantially parallel alignment by swinging them about pivot pin 11 in a clockwise direction, as shown by arrow 34 (FIG. 2). The bar 15 is moved toward the pivot pin 11 and snapped into tongues 12a. Once the bar 15 is in place in tongues 12a, the tension is adjusted by turning knurled knob 24 into the threaded bar 15.

When the user desires to urinate, he presses down on the knurled knob 24, swinging the lower jaw 12 away from the upper jaw 17, allowing pressure on the urethra to be relieved. During the releasing or pivoting-away motion, the user pushes the head of the knurled knob 24 with his thumb while grasping the lower surface of the end of jaw 17. In this way the lower jaw 12 is free to move relative to upper jaw 17. When urination is terminated, the knurled knob 24 may be released, thus pulling the lower jaw 12 into its closed position relative to the entire device 10. Thus, it can be seen that, due to the spring-loaded nature of closure 22, the device can be successfully operated with one hand and at no risk of losing parts of the device.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A device used to electively control incontinent urination in males, comprising:

a) a pair of hinged jaw members having a distal end and forming a clamshell type of restraint for the penis of a human male user, said clamshell type of restraint being able to open and close about said penis, which is disposed therebetween, each of said hinged jaw members rotatively movable with respect to each other, and comprising a cushion member attached thereto, each cushion member being in contact with said penis when said clamshell type of restraint is closed about said penis; and b) an adjustment device carried by said clamshell type of restraint for establishing a predetermined pressure upon the penis, and for preventing urine flow in the urethra of said penis, said adjustment device including spring-loaded biasing means disposed proximate said distal end of said pair of hinged jaw members, operable with one hand for controlling a compressive force upon said hinged jaw members, said adjustment device reestablishing said predetermined pressure upon the penis, after use or removal and replacement of said device, and means disposed proximate said distal end of said pair of hinged jaw members for changing the compressive force exerted by said biasing means, said adjustment device being capable of being manually overridden without releasing, repositioning or removing said device by said human male user thereof, whereby urine flow is electively restricted without appreciably restricting blood flow in said penis, and whereby urine is electively and substantially immediately allowed to flow when said adjustment device is compressed.

2. The device used to control incontinent urination in males in accordance with claim 1, wherein said biasing means of said adjustment device comprises a coil spring located between said adjustment knob and one of said hinged jaw members.

3. The device used to control incontinent urination in males in accordance with claim 2, wherein said adjustment device further comprises a screw attached to said adjustment knob, said adjustment knob for causing said screw to turn, and an adjustment nut for receiving said screw, each of said hinged jaw members comprising means defining an aperture through which said screw passes, and means disposed upon one of said hinged jaw members for restraining said nut against rotation when said screw is turned by said adjustment knob.

4. The device used to control incontinent urination in males in accordance with claim 3, wherein said means defining an aperture in each of said hinged jaw members includes a slot, and further wherein said screw can laterally move in said slot to remove said adjustment nut from its respective restraining hinged jaw member, whereby said clamshell type of restraint may be opened.

5. A device used to control incontinent urination in males, comprising a clamshell type of restraint having clamping members with respective distal ends that are movable between open and closed positions about a penis of an incontinent male, said clamshell restraint having means disposed proximate said distal ends for presetting pressure upon said clamping members to restrict the flow of urine in said penis without appreciably restricting blood flow therein, said means for presetting pressure being capable of substantially immediately reestablishing said preset pressure, notwithstanding use or removal of said device, and said clamshell type of restraint further comprising cushioning means disposed between said clamping members for providing comfort to a clamped penis, wherein said means for presetting pressure may be temporarily manually overridden without releasing, repositioning, resetting or removing said device by a user.

\* \* \* \* \*